United States Patent [19]

Oude Alink

[11] Patent Number: 4,555,576
[45] Date of Patent: Nov. 26, 1985

[54] 4,5-DIHYDROTHIAZOLES AND PREPARATION THEREOF

[75] Inventor: Bernardus A. Oude Alink, St. Louis, Mo.

[73] Assignee: Petrolite Corporation, St. Louis, Mo.

[21] Appl. No.: 612,155

[22] Filed: May 21, 1984

Related U.S. Application Data

[62] Division of Ser. No. 146,905, May 5, 1980, abandoned.

[51] Int. Cl.[4] .............................................. C07D 277/10
[52] U.S. Cl. ....................................... 548/146; 44/63; 252/390
[58] Field of Search .......................................... 548/146

[56] References Cited

U.S. PATENT DOCUMENTS 3,879,524  4/1975  Wehrmeister ...................... 548/146

OTHER PUBLICATIONS

Maguet et al., Bull. Soc. Chim. Fr., 1978, pp. 539–549.

Primary Examiner—Christopher A. Henderson
Attorney, Agent, or Firm—Sidney B. Ring; Leon Zitver

[57] ABSTRACT

2,5-dihydrothiazoles are prepared by reacting aza-alkylene-dienes with sulfur at relatively low temperatures for example below about 160° C. Where the reaction is carried out at relatively higher temperature, for example above about 160° C., such as 160° to 250° C., 4,5-dihydrothiazoles are formed. In addition 2,5-dihydrothiazoles can be converted to 4,5-dihydrothiazoles by heating them to temperatures above about 160° C.

9 Claims, No Drawings

4,5-DIHYDROTHIAZOLES AND PREPARATION THEREOF

This is a division of application Ser. No. 146,905 filed May 5, 1980 now abandoned.

In U.S. Pat. No. 4,106,904 there is described the reaction of aldehyde with ammonia. Where the alpha carbon of the aldehyde is unsubstituted, a cyclic compound is formed in accord with the following equation:

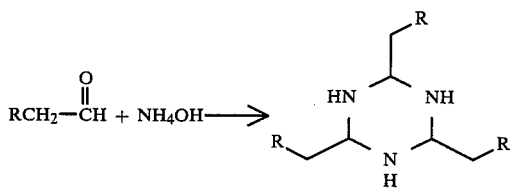

However, as disclosed by Hasek et al, J Org Chem 26, 1822 (1961) where the alpha carbon is substituted non-cyclic, i.e., aliphatic compounds are formed in accord with the following reactions:

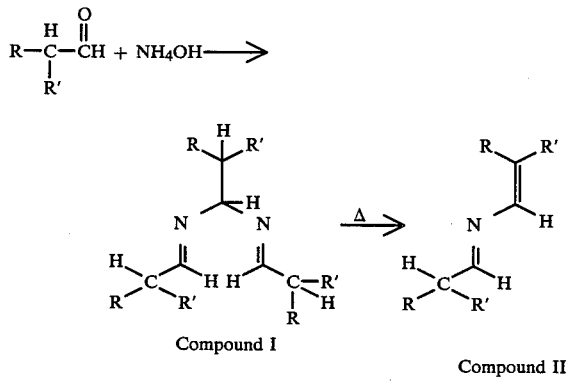

Compound II is the starting material of the present invention. Since Compound I converts substantially quantitatively to Compound II, for purposes of this reaction it is considered an equivalent of Compound II.

In my application. Ser. No. 112,506, filed Jan. 16, 1980, now abandoned where Compounds I and/or II are reacted with sulfur, dihydrothiazoles are formed.

This is illustrated by the following reaction:

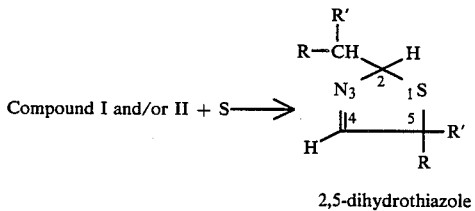

2,5-dihydrothiazole

The reaction is carried out by heating a mixture of Compound I or II and elemental sulfur in stoichiometric amounts at temperatures from 40°–160° C. for 1–24 hrs. Solvents which do not interfere with the reaction may be used but are not necessary.

R and R', which are the moieties of the aldehyde reactant, may be any group which does not interfere with the reaction such as alkyl, cycloalkyl, aryl, aralkyl, alkarylalkyl, etc., but preferably alkyl.

Thus, in the 2,5-dihydrothiazoles of the formula

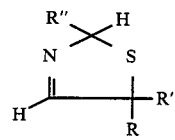

R'' is a branched hydrocarbon, preferably branched alkyl such as

where R and R' have the same meaning as the R and R' groups at position 5.

I have now discovered that the 2,5-dihydrothiazoles of Ser. No. 112,506, now abandoned, can be converted to 4,5-dihydrothiazoles by heating at a higher temperature.

In addition, I have now discovered that instead of separating the 2,5-dihydrothiazoles of Ser. No. 112,506, the reaction of the (1) unsaturated imine and (2) elemental sulfur can be carried out at a higher temperature, for example from about 160° C. or above, such as from about 160°–250° C., until the 4,5-dihydrothiazole is formed.

The reaction is simply carried out by heating 2,5-dihydrothiazoles at temperatures at which the 4,5-dihydrothiazole is formed, for example, from about 160° C. or above, such as about 160°–250° C. for a time sufficient to form the product, such as from about 1–100 hours. The reaction involves a 1,3-prototypic shift. The resulting 4,5-dihydrothiazole has greater hydrolytic stability than the corresponding 2,5-dihydrothiazole.

In cases where the boiling points of the 2,5-dihydrothiazoles are too low to reach the desired reaction temperature, the reaction may be carried out in a pressure reactor such as to allow the compounds to be heated at the desired reaction temperatures.

Isolation of the 2,5-dihydrothiazoles is not necessary. The formation of 4,5-dihydrothiazoles from the imine (1) and sulfur can also be carried out by heating the mixture of the imine (1) and sulfur at temperatures and time shown above. In the reaction $R_1$, $R_2$, $R_3$ and $R_4$ are alkyl, alkylaryl, cycloalkyl, etc.

The reaction is summarized in the following equations:

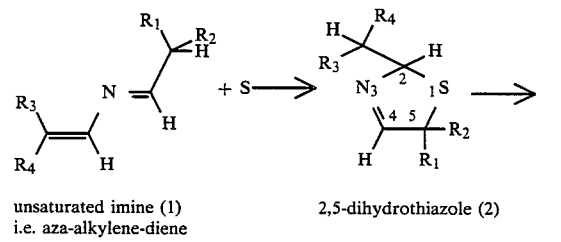

unsaturated imine (1)
i.e. aza-alkylene-diene 2,5-dihydrothiazole (2)

-continued

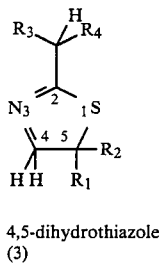

4,5-dihydrothiazole
(3)

The following examples are presented for purposes of illustration and not of limitation.

EXAMPLE 1

3,7-Diethyl-5-azanona-3,5-diene

To a sample of 250 grams of 28% ammonium hydroxide was added 215 grams of 2-ethylbutyraldehyde and the heterogeneous mixture was stirred for 18 hours at ambient temperature. The resulting organic layer was separated, and after drying, slowly distilled at atmospheric pressure to yield 148.8 grams of 3,7-diethyl-5-azanona-3,5-diene. Mass spectrum m/e=181. $^{13}$C nuclear magnetic resonance spectrum, solvent CDCl$_3$, ref. TMS.

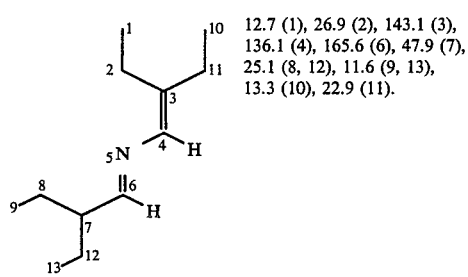

12.7 (1), 26.9 (2), 143.1 (3),
136.1 (4), 165.6 (6), 47.9 (7),
25.1 (8, 12), 11.6 (9, 13),
13.3 (10), 22.9 (11).

EXAMPLE 2

2,5-Dihydro-5,5-diethyl-2-(1-ethylpropyl)thiazole

A sample of 147.8 grams of 3,7-diethyl-5-azanona-3,5-diene, prepared as described in example 1 and 26 grams of elemental sulfur were heated at 150° C. for 19 hours. The resulting product was distilled under diminished pressure and the fraction b.$_{25}$ 145°–150° C., was identified as 128 grams of 2,5-dihydro-5,5-diethyl-2-(1-ethylpropyl)thiazole. Mass spectrum m/e=213, $^{13}$C nuclear magnetic resonance spectrum, solvent CDCl$_3$ ref TMS.

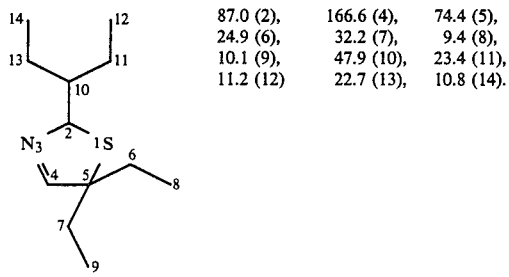

87.0 (2), 166.6 (4), 74.4 (5),
24.9 (6), 32.2 (7), 9.4 (8),
10.1 (9), 47.9 (10), 23.4 (11),
11.2 (12) 22.7 (13), 10.8 (14).

EXAMPLE 3

2,6-Dimethyl-4-azahepta-2,4-diene

To 1400 grams of a 28% solution of ammonium hydroxide was added with stirring over a 4 hour period 1400 grams of isobutyraldehyde while a reaction temperature of 22°–47° was maintained. After completion of the addition stirring was continued for 18 more hours. The resulting organic layer was refluxed under azeotropical conditions until ammonia evolution ceased (14 hours). The resulting 1137.8 grams of product was identified as 2,6-dimethyl-4-azahepta-2,4-diene. Mass spectrum m/e=125. $^{13}$C nuclear magnetic resonance spectrum, solvent CDCl$_3$, reference TMS.

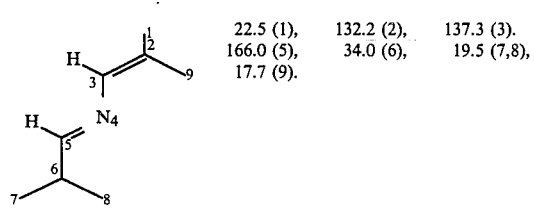

22.5 (1), 132.2 (2), 137.3 (3).
166.0 (5), 34.0 (6), 19.5 (7,8),
17.7 (9).

EXAMPLE 4

2,5-Dihydro-5,5-dimethyl-2-(1-methylethyl)thiazole

A mixture of 364.9 grams of 2,6-dimethyl-4-azahepta-2,4-diene prepared as described in example 2 and 93.6 grams of elemental sulfur was heated for 6 hours at 145° C. The resulting product was distilled under diminished pressure and the fraction b.$_{25}$ 91°–93° C. was identified as 280 grams of 2,5-dihydro-5,5-dimethyl-2-(1-methylethyl)thiazole. Chemical ionization mass spectroscopy m/e=157, 142, 124, 114, 90, 86. $^{13}$C nuclear magnetic resonance spectrum, solvent CDCl$_3$ ref. TMS.

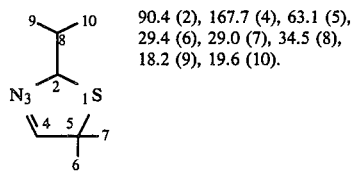

90.4 (2), 167.7 (4), 63.1 (5),
29.4 (6), 29.0 (7), 34.5 (8),
18.2 (9), 19.6 (10).

Using the procedures of examples 2 and 4, several other substituted 2,5-dihydrothiazoles were prepared from the corresponding unsaturated imines. The results are summarized in Table I.

TABLE I

| Example No. | Starting imine | Product |
| --- | --- | --- |
| 5 | 4,9-Diethyl-7-azatrideca-5,7-diene | 2,5-Dihydro-5-butyl-5-ethyl-2(1-ethylpentyl)thiazole |

TABLE I-continued

| Example No. | Starting imine | Product |
|---|---|---|
| 6 | 3,7-Dimethyl-5-azanona-3,5-diene | 2,5-Dihydro-5-ethyl-5-methyl 2-(1-methylpropyl)thiazole |

EXAMPLE 7

4,5-Dihydro-5,5-dimethyl-2-(1-methylethyl)thiazole

A sample of 165 g of the product prepared in example 4 was placed in an autoclave. The closed autoclave was heated with stirring to 205° C. and kept at this temperature for 21 h. The autogeneous pressure reached a maximum of 85 psi. After cooling to ambient temperature, 165 g of product was isolated. A sample of 161 g of product was treated with 20% HCl. The acid insoluble portion was taken up in ether and the ethereal solution evaporated under diminished pressure to yield 66.4 g of mainly isopropyldisulfide. $^{13}$C nmr (CDCl$_3$).

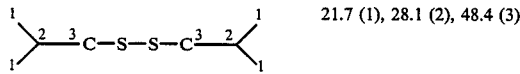

21.7 (1), 28.1 (2), 48.4 (3)

The acid solution was basified and extracted with ether. The ethereal solution after evaporation yielded 54.6 g of 4,5-Dihydro-5,5-dimethyl-2-(1-methylethyl)-thiazole, $^{13}$C nmr (CDCl$_3$).

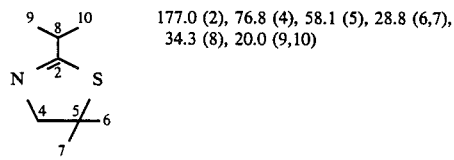

177.0 (2), 76.8 (4), 58.1 (5), 28.8 (6,7), 34.3 (8), 20.0 (9,10)

EXAMPLE 8

4,5-Dihydro-5,5-diethyl-2(1-ethylpropyl)thiazole

A sample of 17 g of the product described in example 2 was heated for 18 h. at 220° C. The resulting product was worked up as described in example 7 to yield 9 g of 4,5-Dihydro-5,5-diethyl-2(1-ethylpropyl)thiazole. $^{13}$C nmr (CDCl$_3$).

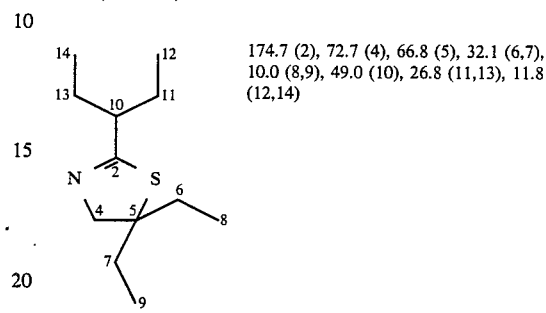

174.7 (2), 72.7 (4), 66.8 (5), 32.1 (6,7), 10.0 (8,9), 49.0 (10), 26.8 (11,13), 11.8 (12,14)

Using the process described in example 7, the 2,5-dihydrothiazoles listed in Table I were converted to 4,5-dihydrothiazoles. The results are summarized in Table II:

TABLE II

| Example No. | Starting Thiazole | Product |
|---|---|---|
| 9 | 2,5-Dihydro-5-butyl-5-ethyl-2(1-ethylpentyl)thiazole | 4,5-Dihydro-5-butyl-5-ethyl-2(1-ethylpentyl)thiazole |
| 10 | 2,5-Dihydro-5-ethyl-5-methyl 2-(1-methylpropane)thiazole | 4,5-Dihydro-5-ethyl-5-methyl 2-(1-methylpropane)thiazole |

The compositions of this invention have a wide variety of uses. For example, they are useful as corrosion inhibitors, antioxidants, fuel oil additives, etc.

I claim:

1. A process of preparing a 4,5-dihydrothiazole which comprises heating to a temperature above 160° C., a 2,5-dihydrothiazole or a mixture comprising an aliphatic aza-alkylene diene and sulfur which is a precursor thereof.

2. A process of preparing a 4,5-dihydrothiazole of the formula

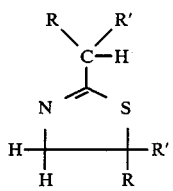

which comprise heating to a temperature above 160° C. a 2,5-dihydrothiazole of the formula

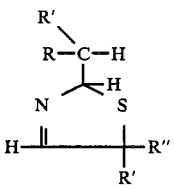

or a mixture comprising an aza-alkylene-diene of the formula

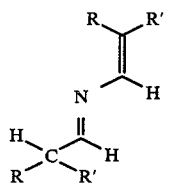

and sulfur where R and R' are independently selected from the group consisting of alkyl, cycloalkyl, aryl, aralkyl and alkarylalkyl.

3. The process of claim 2 where R and R' are alkyl.

4. The process of claim 2 where R and R' are lower alkyl.

5. The process of claim 4 where the alkyl groups are ethyl, methyl, or butyl or combinations thereof.

6. The process of claim 5 where the aza-alkylene-diene reacted is

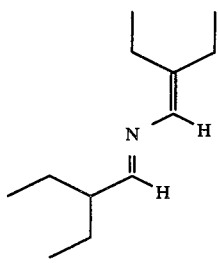

and the 4,5-dihydrothiazole produced is

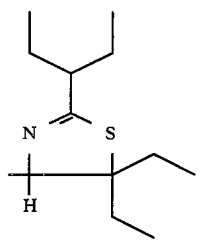

7. The process of claim 5 where the aza-alkylene-diene reacted is

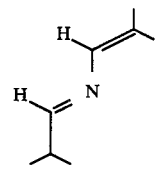

and the 4,5-dihydrothiazole produced is

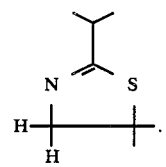

8. The process of claim 5 where the aza-alkylene-diene reacted is

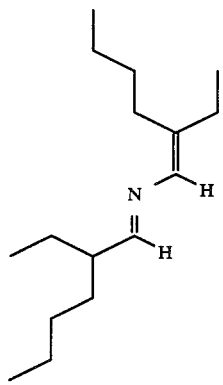

and the 4,5-dihydrothiazole produced is

9. The process of claim 5 where the aza-alkylenediene reacted is
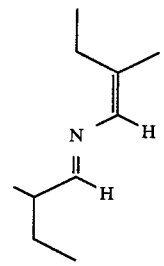
and the 4,5-dihydrothiazole produced is
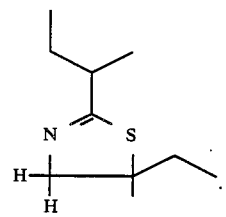
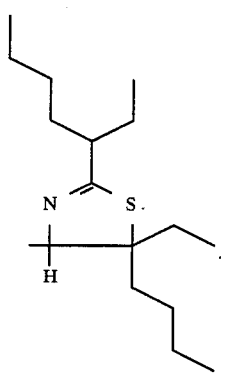
* * * * *